Figure 1:
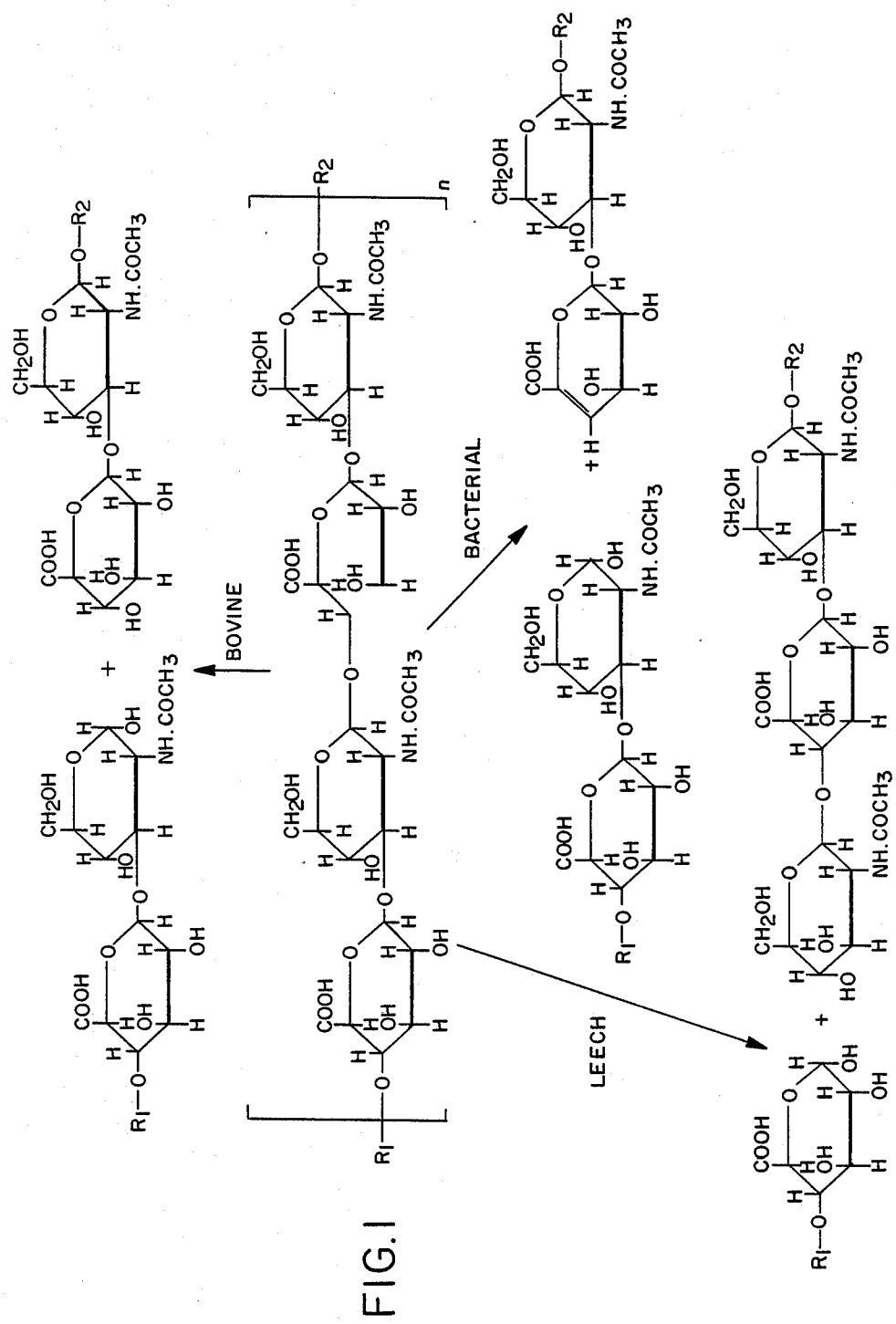

United States Patent [19]

Sawyer et al.

[11] Patent Number: 4,820,516

[45] Date of Patent: Apr. 11, 1989

[54] HYALURONIDASE

[75] Inventors: Roy T. Sawyer; Jeffrey Edwards, both of Swansea, United Kingdom

[73] Assignee: Biopharm (UK) Limited, Swansea, United Kingdom

[21] Appl. No.: 829,785

[22] Filed: Feb. 14, 1986

[30] Foreign Application Priority Data

Feb. 16, 1985 [GB] United Kingdom ............... 8504025

[51] Int. Cl.$^4$ ............................................. A61K 37/54
[52] U.S. Cl. .................. 424/94.62; 435/201; 514/912; 514/913
[58] Field of Search ............ 424/94.62; 435/201; 514/912, 913

[56] References Cited

U.S. PATENT DOCUMENTS 4,534,967  8/1985  Jacobson et al. .................... 424/95

OTHER PUBLICATIONS

R. T. Sawyer, *North American Freshwater Leeches* (Urbana, IL: Univ. of Illinois Press), pp. 66–69, 72.
R. T. Sawyer, *Leech Biology and Behaviour*, vol. II, (Oxford: Clarendon Press, 1986), p. 496.
Linker et al., reported in *Nature*, 180:810–811 (1957).
Linker et al., "The Production of Hyaluronate Oligosaccharides . . . ", *J. Biol. Chem.*, 235:924–927 (1960).
Budds et al., "A Comparison of the Properties of the Hyaluronidases . . . ", *Comp. Biochem. Physiol.* 87B:497–500 (1987).
H. Yuki et al., *J. Biol. Chem.* 248(5):1878–1879, 1963.

*Primary Examiner*—John Rollins
*Attorney, Agent, or Firm*—Bert J. Lewen; Henry Sternberg

[57] ABSTRACT

The hyaluronidase, which is a hyaluronic acid-specific endo-$\beta$-glucuronidase, having a molecular weight of about 28,500 in non-reduced form, is derived from buffalo leeches (that is, leeches of the sub-family Hirudinariinae, such as the species *Hirudinaria manillensis* or *Poecilobdella granulosa*).

The hyaluronidase, which cleaves hyaluronic acid, but not chondroitin, chondroitin -4- sulphate, chondroitin -6- sulphate or heparin, is considerably more stable at high temperatures and extremes of pH than known leech hyaluronidase. It has a wide range of uses where breakdown of hyaluronic acid is required; of particular interest is in pharmaceutical or veterinary formulations, either as an active agent or a spreading or percutaneous factor. The hyaluronidase is useful for stimulating flow of physiological fluids in the eye (for example, in the treatment of glaucoma).

17 Claims, 4 Drawing Sheets

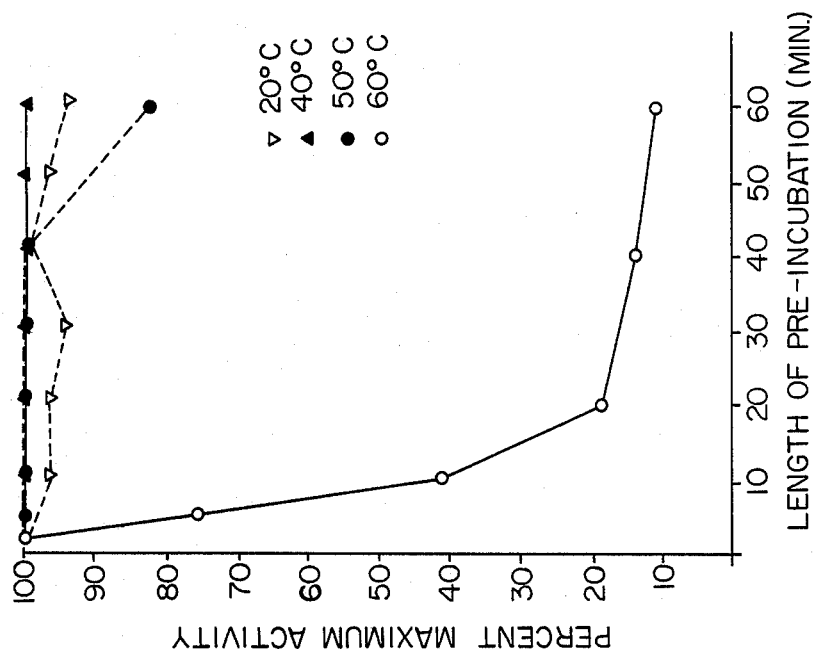
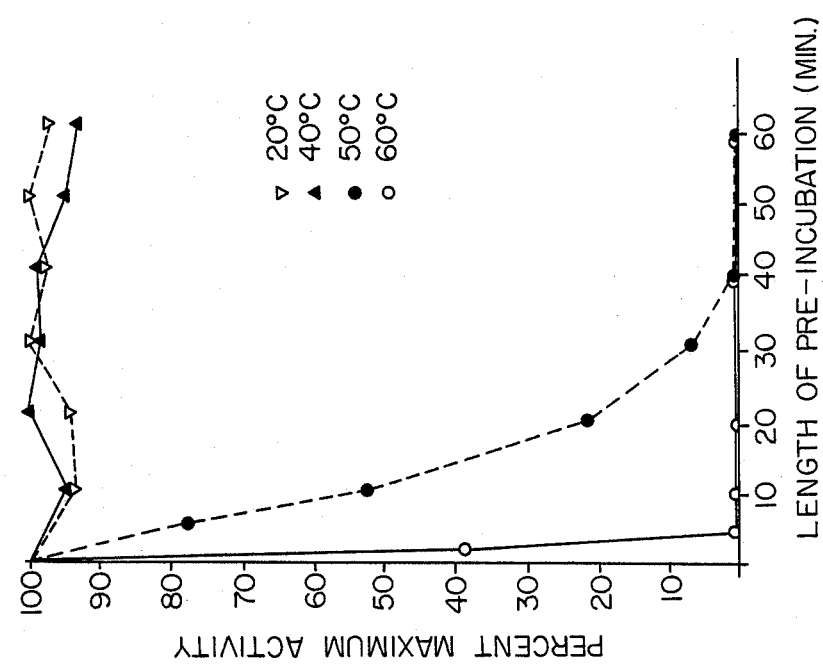

HYALURONIDASE

The present invention is concerned with hyaluronidases.

The name hyaluronidase is used for an important group of enzymes which degrade certain tissues polysaccharides (glycosaminoglycans). There are basically two types of hyaluronidases: (a) those which are relatively non-specific and cleave hyaluronic acid, chondroitin and related polysaccharides; and (b) those which specifically cleave hyaluronic acid.

Hyaluronic acid is a polysaccharide widely found in the extracellular connective tissue of animals. As the "cement" which binds cells together, the main constituent of the vitreous of the eye, and functionally important in joints, etc, hyaluronic acid is of considerable physiological importance. An enzyme which specifically cleaves hyaluronic acid should have a wide variety of medical and scientific applications.

Hyaluronidases are widely distributed in nature in for example, mammalian testes, liver and spleen and in certain microorganisms. Mammalian hyaluronidases are of the first type; that is, they cleave (non-specifically) hyaluronic acid, chondroitin and other polysaccharides.

Other hyaluronidases of the second type (that is, hyaluronic acid specific), are derived from microorganisms such as streptomcyces bacteria or from the leech *Hirudo medicinalis*, as described by Linker et al, 1960 J. Biol. Chem 235 pp 924–7. The hyaluronidase derived from *Hirudo medicinalis* has a different mechanism for cleaving hyaluronic acid from microorganism-derived hyaluronidases, as illustrated in FIG. 1 of the accompanying drawings. Specifically, the hyaluronidase derived from *Hirudo medicinalis* is an endo-$\beta$-glucuronidase (see the above-mentioned article by Linker et al). This is the only reported example of which we are aware of a hyaluronic acid-specific endo-$\beta$-glucuronidase.

The $\beta$-glucuronidase identified by Linker et al has been further characterised by Yuki and Fishman (1963 J. Biol Chem 238 pp 1877–9) as having optimum activity at pH 6.0. There has been little subsequent published work concerning the hyaluronidase derived from *Hirudo medicinalis*.

FIG. 1 shows the mode of action of different hyaluronidases on hyaluronic acid. Only leech hyaluronidase has endo-$\beta$-glucuronidase activity.

FIG. 2 shows the thermal stability of hyaluronidase. FIG. 2(A) shows hyaluronidase derived from *Hirudo medicinalis* and FIG. 2(B) from *Poecilobdella granulosa*. In both instances the hyaluronidase was preincubated for different time intervals at 20°, 40°, 50° and 60° C. before assaying at 37° C.

Figure 3B:
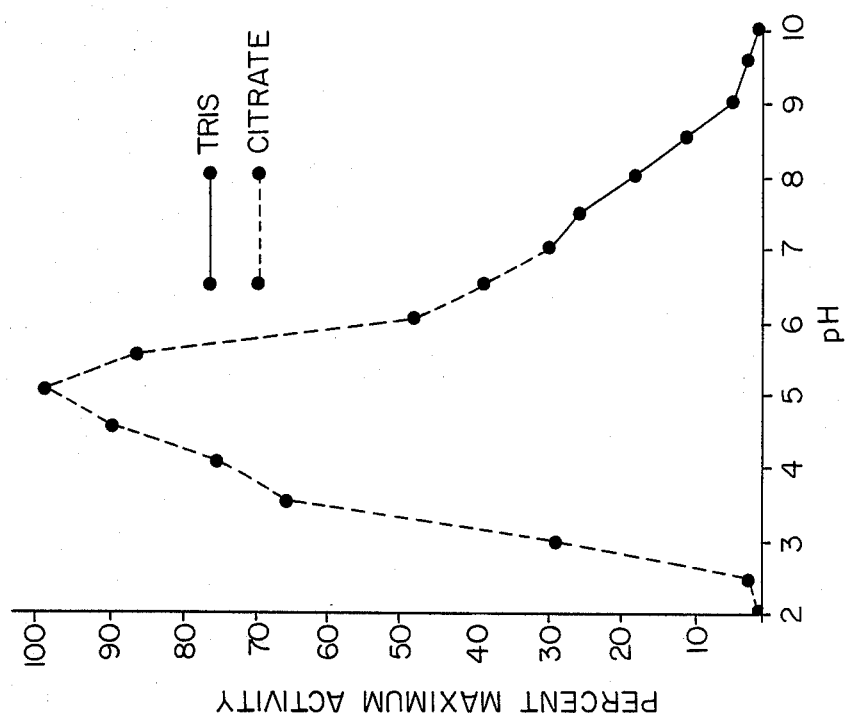
Figure 3A:
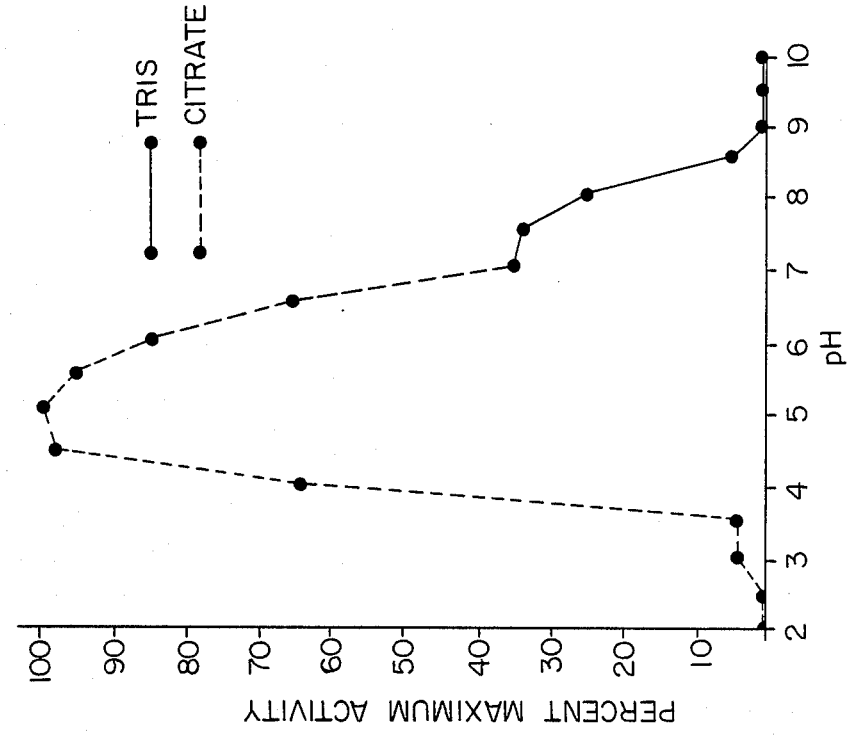

FIG. 3 shows the activity of hyaluronidase. FIG. 3(A) shows the activity of *Hirudo medicinalis* and FIG. 3(B) of *Poecilobdella granulosa*. In both instances the hyaluronidase was incubated at 37° C. between a pH of 2.0 and 10.0.

Figure 4:
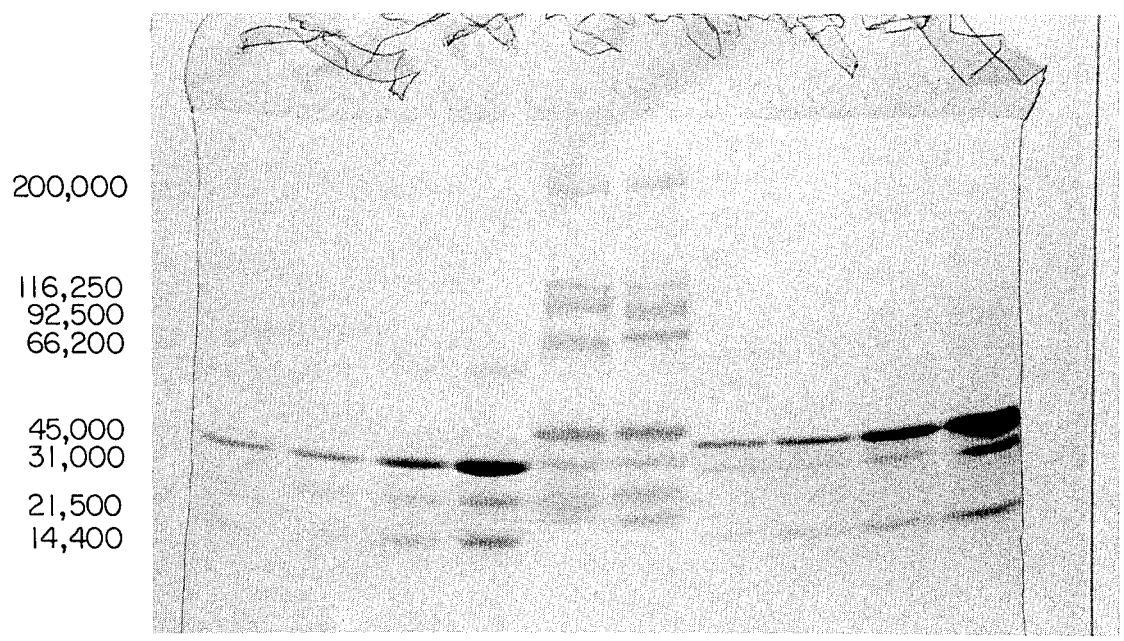

FIG. 4 shows an electrophoresis gel (3–15% SDS-PAGE) demonstrating the molecular weight analysis of buffalo leech hyaluronidase, indicating that the non-reduced form has a molecular weight of 28,500 Daltons and the reduced form of 40,000 Daltons. Lanes 1–4 show the result of 5 $\mu$l, 10 $\mu$l, 20 $\mu$l and 50 $\mu$l, respectively, of the non-reduced enzyme preparation. Lane 5 shows the non-reduced molecular standards and Lane 6 shows the reduced molecular standards. Lanes 7–10 show 5 $\mu$l, 10 $\mu$l, 20 $\mu$l and 50 $\mu$l enzyme preparations, respectively, reduced and alkylated.

We have now isolated a novel hyaluronic acid-specific endo-$\beta$-glucuronidase from buffalo leeches (the term "buffalo leech") is a broad term comprising the sub-family Hirudinariinae; that is, the genera Hirudinaria, Illebdella and Poecilodbella, as defined in "Leech Biology and Behaviour" by Dr. R. T. Sawyer, Oxford University Press, 1986.

According to the invention, therefore, there is provided an endo-$\beta$-glucuronidase derived from leeches of the sub-family Hirudinariinae.

The endo-$\beta$-glucuronidase according to the invention is hyaluronic acid specific (that is, capable of cleaving hyaluronic acid, but not chondroitin, chondroitin-4-sulphate, chondroitin-6-sulphate or heparin). Furthermore, the enzyme has been found to be incapable of cleaving fibronectin, and is therefore considered to be substantially free of protease activity. The known endo-$\beta$-glucuronidase derived from *Hirudo medicinalis* is also hyaluronic acid specific, but the endo-$\beta$-glucuronidase according to the invention differs from the known endo-$\beta$-glucuronidase in that it is demonstrably a much more stable, and therefore useful, molecule, under conditions such as high temperature and extremes of pH.

The endo-$\beta$-glucuronidase derived from the buffalo leech is characterised by improed heat stability compared with that derived from *Hirudo medicinalis*; specifically, endo-$\beta$-glucuronidase derived from buffalo leech retains at least 70% of its activity (when assayed at 37° C.) after incubation for 30 minutes at 50° C. (FIG. 2). In comparison, endo-$\beta$-glucuronidase derived from *Hirudo medicinalis* loses in excess of 90% of its activity on incubation under the same conditions. This is illustrated in FIG. 2 of the accompanying drawings. Furthermore, the enzyme from the buffalo leech retains at least 30% of its activity at 50° C. over 12 hours, whereas that from *Hirudo medicinalis* is completely inactivated after 40 minutes.

The endo-$\beta$-glucuronidase derived from the buffalo leech is further characterised by improved activity under extreme pH conditions compared with that derived from *Hirudo medicinalis*. This is illustrated in FIG. 3 of the accompanying drawings which is a graph of activity against pH for an endo-$\beta$-glucuronidase according to the invention, compared with one derived from *Hirudo medicinalis*. Specifically, at pH 3.5 the endo-$\beta$-glucuronidase from the buffalo leech retains at least 50% ot its activity, whereas that derived from *Hirudo medicinalis* retains less than 10% of its activity. Similarly at pH 9.0, the enzyme from the buffalo leech retains 5% of its activity whereas that from *Hirudo medicinalis* is completely inactivated. Furthermore, at pH 9.0 Hirudo enzyme is irreversibly inactivated, whereas that from the buffalo leech still retains activity when subsequently assayed at optimal pH.

The endo-$\beta$-glucuronidase derived from buffalo leeches is still further characterised by its behaviour in the presence of $HgCl_2$. At low concentrations (10 $\mu$M $HgCl_2$), the endo-$\beta$-glucuronidase derived from buffalo leeches was substantially completely inactivated, whereas under the same conditions, the endo-$\beta$-glucuronidase derived from *Hirudo medicinalis* retained 50% of its activity.

Neither the endo-$\beta$-glucuronidase derived from buffalo leeches (which may be, for example, of the species *Hirudinaria manillensis* or *Poecilobdella granulosa*), nor the known endo-$\beta$-glucuronidase derived from *Hirudo*

*medicinalis*, was inhibited by millimolar saccharo-1, 4 lactone; that is in contradistinction to known β-glucuronidases (see pp 361–409 of Vol 16 of Advances in Enzymology, Beta-glucuronidases, Interscience, London by W H Fishman).

The endo-β-glucuronidase according to the invention has been found to comprise a polypeptide of molecular weight 28,500±3,000 (in non-reduced form), when measured by sodium dodecyl sulphate-polyacrylamide electrophoresis using a polyacrylamide gel of gradient 3 to 15%. This is a low molecular weight compared with molecular weights of other hyaluronidases. Such a molecular weight corresponds to about 285 amino acid units, which makes the endo-β-glucuronidase particularly suitable for syntheses, manipulation or modification by either protein engineering or genetic engineering. The present invention accordingly further comprises the synthetic enzyme corresponding to the endo-β-glucuronidase isolated from buffalo leeches and having substantially the same characteristics and activity, particularly with respect to its hyaluronic acid specificity. (Where we refer herein to endo-β-glucuronidase derived from buffalo leeches, of course, we intend to encompass the genetically engineered material which is inevitably "derived from" the leech in the sense that it is first necessary to have a source of the enzyme isolated from the leech before further enzyme can be genetically engineered either directly from leech derived DNA or RNA, or indirectly by means of a synthetic gene encompassing all or part of the original DNA sequence.)

The endo-β-glucuronidase derived from the buffalo leech further differs from that derived from *Hirudo medicinalis* in its degree of activity.

The activity of an endo-β-glucuronidase can be expressed in standard units; one unit corresponds to the reducing power of glucuronic acid (glucose equivalent in micrograms) liberated per hour from hyaluronic acid at optimum pH. The endo-β-glucuronidase according to the invention has an activity of approximately 3500 units per leech (compared with about 233 units per leech reported for the hyaluronidase isolated from *Hirudo medicinalis*).

As indicated, the endo-β-glucuronidase according to the invention is highly specific for and highly active against, hyaluronic acid. Such a potent and stable enzyme has a variety of possible uses, as follows:

(a) To identify and quantify hyaluronic acid, either by itself or linked with a marker molecule (immunofluorescent, colloidal gold, etc) or by means of an enzyme (or other) system of amplification. When carefully quantified the endo-β-glucuronidase according to the invention could be the active ingredient in a diagnostic test for hyaluronic acid. Such tests would be useful, for example, in in vivo or in vitro monitoring or diagnosing (1) bacteria, such as Streptococcus, encapsulated with hyaluronic acid; and (2) rheumatoid arthritis, liver disease, bladder carcinoma, Wilms tumour and other diseases characterised by elevated levels of hyaluronic acid. That hyaluronic acid in body fluids can be assayed using the endo-β-glucuronidase according to the invention is illustrated in Example 2.

(b) Owing to the unique cleavage mechanism, the endo-β-glucuronidase according to the invention would be useful in synthesis for obtaining novel breakdown products of hyaluronic acid, which could be used in synthesis for the production of highly pure hyaluronic acid.

(c) As a standard assay to monitor commercially prepared hyaluronic acid, which would be of interest to regulatory authorities as well as producers of hyaluronic acid.

(d) For removing hyaluronic acid from commercially coated objects, such as prosthetic devices, and for aiding removal of glycosamine-based deposits (for example, from teeth or contact lenses, or as an active ingredient in biological detergents).

(e) In studying the role of, and manipulating, glyosaminoglycans, in cell-cell and cell-substratum interactions, and other cell culture work (where the ability to degrade hyaluronic acid selectively is a considerable advantage). This application wound include use on an industrial scale, such as large scale culture of mammalian and other cells from which products are derived.

(f) In the potentiation of formulations applied to plant, animal, or microbial matter (such as antibacterial formulations e.g. against Streptococcus bacteria in vivo and in vitro).

(g) In improving fertilization in vivo or in vitro (e.g. when the endo-β-glucuronidase is injected before the sperm in artificial insemination), in vitro fertilization or in the separation of fish spawn.

(h) In treatment of meat, fur or animal hide, such as in leather production.

(i) For the isolation, extraction or purification of hyaluronic acid (such as part of an affinity chromatography system).

(j) In pharmaceutical or verterinary therapy.

In connection with use in therapy, the endo-β-glucuronidase according to the invention generally acts as a dispersal agent (or spreading factor) or aids penetration through the skin (a percutaneous factor). The present invention further comprises a pharmaceutical or veterinary formulation comprising a hyaluronic acid-specific endo-β-glucuronidase and an acceptable diluent, carrier or excipient. Examples of such pharmaceutical or veterinary uses include, but are not restricted to the following:

1. As an adjunct to the injection of other substances (such as local anaesthetic), or whenever an intramuscular or subdermal injection is indicated (eg for patients on a subdermal intramuscular "drip" to assist in the initial dispersal of fluids from the site of injection).

2. For treatment of blood insufficiency in the heart to reduce acute myocardial ischaemia or infarction.

3. For the treatment of skin and tissue grafts, or flaps, such as commonly encountered in plastic and microsurgery, to remove congestion and improve circulation.

4. For treatment of glaucoma and other eye disorders in which some dissolution of the vitreous or improvement of circulation of physiological fluids in or about the eye would be useful; for example, to assist in the non-surgical removal of various obstructions, or to alleviate intraocular pressure, thrombosis in the eye, and in the treatment of detached or impending detached retinas. The latter therapeutic use (that is the treatment of glaucoma and other eye diseases) has, to our knowledge, never previously been suggested for an endo-β-glucuronidase.

5. As a novel drug delivery system through the skin, mucus membranes or similar means of penetrating from outside into the body matrix; for example, as a topical or percutaneous agent applied onto the skin either by itself or as an adjunct, as an aerosol inhalation to penetrate into the nasal membranes, as an adjunct applied to the cornea or other parts of the eye. This is therapeutic use (as a drug delivery system) as far as we known this has never previously been suggested.

6. As an antibiotic to remove or weaken the hyaluronic acid capsule surrounding certain pathogenic microorganisms, such as Streptococcus-associated periodontal diseas and streptococcal pneumonia; and as an adjunct in such cases to other antibiotics directed towards the same microorganisms.

7. As an agent to remove or weaken the hyaluronic acid capsule surrounding certain tumours and cancerous growths; and as an adjunct in such cases to chemotherapy directed towards the same tumours.

8. As an inhibitor of angiogenesis; this would be useful for example as an anticancer agent.

In order that the present invention may be more fully understood, the following Examples are given by way of illustration only.

EXAMPLE 1

The head region of a buffalo leech of the species *Hirudinaria manillensis* was removed and homogenised in distilled water. The supernatant was saved, while the precipitate was resuspended and centrifuged again. The supernatants were combined to give stage I enzyme.

Stage II was prepared by adding 40% saturated ammonium sulphate to stage I supernatant; centrifuging the suspension at 800 g for 20 minutes at 4° C., and then adding to the resultant supernatant ammonium sulphate to 80% saturation. The suspension was centrifuged at 800 g for 20 minutes at 4° C.; the pellet being resuspended in a 50% saturated solution of ammonium sulphate, and centrifuged at 800 g for 20 minutes at 4° C. The supernatant was then dialyzed three times against distilled water at 4° C., the dialysate being centrifuged at 2600 g for 20 minutes at 4° C. to remove precipitates, resulting in stage II enzyme. A percentage yield of 20% from stage I to stage II was obtained.

The resulting hyaluronidase was a remarkably stable enzyme which retained its activity following a diversity of storage conditions:

| Purity | Storage conditions | Time of storage | % of original activity |
| --- | --- | --- | --- |
| stage I | −20° C. | 7 days | 106% |
|  | −20° C. | 47 days | 132% |
| stage II | −20° C. | 21 days | 95% |
| stage I (freeze dried) | 4° C. | 29 days | 82% |
| stage II (freeze dried) | −20° C. | 20 days | 109% |

After one year in the freezer, stage II preparation retains 50% of its activity.

Increased activity following freezing is interpreted as physical release of enzyme from encapsulating granules, or similar phenomenon. The hyaluronidase has optimum activity in the pH range 4.5 to 5.5 (malic acid) with ionic strength in the range 0.1–0.2 molar and was specific for hyaluronic acid.

The mode of action of the hyaluronidase was examined in a test in which the total reducing sugar was detected by the 3,5-dinitrosalicylic acid assay. The resultant reducing sugar produced by the enzyme action was not N acetylhexosamine (detected by the method of Reising et al). In other words the hyaluronidase derived from the buffalo leech lacked the endo-β-N-acetylhexosaminidase action typical of mammalian hyaluronidase. These tests demonstrate that the hyaluronidase is different from mammalian and streptomyces hyaluronidase and hydrolyzes the internal glucuronic bonds of hyaluronic acid; that is, it was an endo-β-glucuronidase.

EXAMPLE 2

Analysis of Hyaluronic Acid in Body Fluids

After incubation of endo-β-glucuronidase with urine at 37° C. for 1 hour, the hyaluronic acid content was measured by assay of the glucose reducing equivalents released during the incubation. Measurements of between 40 and 80 g hyaluronic acid per ml urine were routinely obtained. Before incubation the urine was first dialysed against distilled water at 4° C. for 24 hours to remove all reducing sugars.

The enzyme was stable for at least 4 hours in dialysed or undialysed urine and did not require the presence of a buffering material for near-maximal activity.

The endo-β-glucuronidase according to the invention can be used in assaying levels of hyaluronic acid of a variety of body fluids including urine, plasma, saliva, synovial fluid and aqueous humor.

EXAMPLE 3

The molecular weight of the hyaluronidase was determined by treatment with sodium dodecyl sulphate (SDS) followed by polyacrylamide gel electrophoresis.

Samples (5000 units per ml) of hyaluronidase derived from *Poecilobdella granulosa*, were heated at 100° C. for 3 minutes in the presence of SDS. Aliquots of this mixture (5–50 μl) were then run on a 3–15% polyacrylamide gel (FIG. 4). suitable markers of known molecular weight were simultaneously run on adjacent lanes in the gel, in order to obtain an accurate estimate of the molecular weight of the hyaluronidase.

A measurement of 28,500±3,000 daltons was obtained for the protein in the sample which represented 80% of the total protein. In order to ensure that this protein was the hyaluronidase, a sample of hyaluronidase which had not been heated to 100° C. in SDS was run on a 7% resolving gel which was overlaid with 0.5 mg per ml hyaluronic acid. Digestion of hyaluronic acid was followed by use of Alcian blue, a dye by which hyaluronic acid is detectable as a blue stain.

The protein responsible for hyaluronic acid digestion in the gel (indicated by the lack of blue stain) was excised from the gel, minced and heated with SDS at 100° C. It was then run adjacent to a control sample of SDS hyaluronidase.

The protein responsible for hyaluronic acid digestion was found to correlate with that at 28,500±3,000 daltons.

EXAMPLE 4

(a) Temperature stability

Samples of hyaluronidase derived either from buffalo leech or *Hirudo medicinalis* each containing 2000 units were incubated at 50° C. or 60° C. At various times aliquots were taken and subsequently assayed for hyaluronidase activity by incubation for 1 hour at 37° C. at pH 5.0 (20 mm- Na citrate, 0.1M-Na Cl, 1 mg per ml hyaluronic acid). Activity was assayed by measurement of glucose reducing equivalents released by hyaluronic acid digestion. Results (FIG. 2) showed that the enzyme derived from the buffalo leech was significantly more thermostable than that from *Hirudo medicinalis*.

After preincubation for 30 minutes at 50° C., the buffalo leech hyaluronidase retained at least 70% of its activity whereas that from *Hirudo medicinalis* lost in excess of 90% of its activity.

Similarly, after preincubation at 60° C. for 10 minutes the hyaluronidase from the buffalo leech retained at least 25% of its activity while that from *Hirudo medicinalis* was completely abolished.

(b) pH Dependence

Samples of hyaluronidase derived either from buffalo leech or *Hirudo medicinalis* each containing 500 units were incubated at 47° C. for 1 hour at a range of pHs from 2.0 to 10.0 (20 mM-Na citrate for pH 2 to 7, 20 mM-Tris Hcl for pH 7-10). All incubation mixtures contained 0.1M-NaCl, 1 mg per ml hyaluronic acid.

At both acid and alkaline extremes of pH an inhibition of activity was observed in the activity of both hyaluronidases. The extent of the inhibition and its reversibility differed substantially however between the two enzymes.

That from buffalo leecH retained at least 50% of its maximal activity at pH 3.5 whereas that from *Hirudo medicinalis* retained less than 10% of its activity. Similarly at pH 9.0 the enzyme from the buffalo leech retained 5% of its activity while that from *Hirudo medicinalis* was completely inactivated.

To assess whether the inhibition of the enzymes at pH 9.0 represented irreversible inactivation the mixtures at pH 9.0 were subsequently brought to pH 5.0 and reincubated at 37° C. for 1 hour. WheN then assayed for glucose reducing equivalents produced, it was found that the hyaluronidase activity from the buffalo leech was still present while that from *Hirudo medicinalis* had been irreversibly abolished.

EXAMPLE 5

The head region of 40 buffalo leeches of the species *Poecilobdella granulosa* were removed and weighed (32.8 g fresh weight). They were then homogenised in distilled water for 10 minutes at 4° C. The mixture was then centrifuged at 800 g for 20 minutes at 4° C. The supernatant was decanted and the pellet extracted twice again with distilled water. The supernatant were pooled and formed the stage I.

Stage II was prepared by adding 40% saturated ammonium sulphate to stage I supernatant; centrifuging the suspension at 800 g for 20 minutes at 4° C., and then adding to the resultant supernatant ammonium sulphate to 80% saturation. The suspension was centrifuged at 800 g for 20 minutes at 4° C.; the pellet being resuspended in a 50% saturated solution of ammonium sulphate, and centrifuged at 800 g for 20 minutes at 4° C. The supernatant was then dialyzed three times against distilled water at 4° C., the dialysate being centrifuged at 2600 g for 20 minutes at 4° C. to remove precipitates, resulting in stage II enzyme. A percentage yield of 20% from stage I to stage II was obtained.

Similar results were obtained when the enzyme was extracted from non-cephalic tissue.

The activity measured at each step and the recovery as a percentage of the activity at stage I are given below.

| Purity | Total activity (units) | % of original activity |
|---|---|---|
| Stage I | 191486 | 100 |
| 40% AS | 172167 | 90 |
| 80% AS | 113357 | 59 |
| Stage II | 77736 | 41 |

Activity of the hyaluronidase was measure by incubation at 37° C. for 1 hour in 20 mM-Na citrate, 0.1M-NaCl and 1 mg per ml hyaluronic acid. One unit is defined as that amount of enzyme activity that produces 1 $\mu$g of glucose reducing equivalents from hyaluronic acid in 1 hour at 37° C.

To further purify the stage II enzyme samples containing 15,000 to 20,000 units were applied to a Sephadex G100 column (height 93 cm, volume 187 cm$^3$). The column was eluted with 50 mM-Tris HCl pH 7.0, 20 mM-NaCl at 1.6 ml per mimute at an operating pressure of 108 cm H$_2$O. The hyaluronidase was eluted between 65 minutes and 105 minutes with a peak of maximal activity obtained at 85 minutes.

Recoveries off the column were between 90% and 110%. The fraction collected represented stage III.

Typical examples of the specific activity of the enzyme per mg protein are given below.

|  | Specific activity (units per mg protein) |
|---|---|
| Stage I | 200 |
| Stage II | 530 |
| Stage III | 1200 |

EXAMPLE 6

Vitreous humors of cows' eyes were removed and suspended separately in 20 mM-MES, 0.1M NaCL pH 5.0 in a final volume of 10 ml. Measurement of the glucose reducing equivalents present initially gave a reading of zero. The mean fresh weight of each humor was 2.75 g.

To one humor 5000 units of hyaluronidase from buffalo leech was added. To another was added 5000 units of hyaluronidase as well as 2 mg hyaluronic acid. The latter was used as a control to determine that digestion of hyaluronic acid could occur under the in vivo conditions of the incubation.

After incubation for one hour at 37° C. the mixture containing humor incubated solely with hyaluronidase contained a total of 3.38 mg glucose equivalents while the other with added hyaluronic acid contained 4.68 mg. These results confirm that presence of significant amounts of hyaluronic acid in the vitreous humor which can be digested by a hyaluronidase of the endo-$\beta$-glucuronidase type. This accords with use of the enzyme as a therapeutic agent in the treatment of hyaluronic acid-related eye disorders.

We claim:

1. A hyaluronic acid-specific endo-$\beta$-glucuronidase derived from the leech of the sub-family Hirudinariinae.

2. A hyaluronic acid-specific endo-$\beta$-glucuronidase capable of cleaving hyaluronic acid, but not chondroitin, choindroitin-4-sulphate, or chondroitin-6-sulphate and having a molecular seight in non-reduced form of 28,500±3,000 when measured by sodium dodecyl sulphate-polyacrylamide electrophoresis, said endo-$\beta$-glucuronidase being such that it retains at least 70% of its activity at 37° C. after having been incubated for 30 minutes at 50° C. and at least 55% of its activity in an aqueous medium at pH 3.5.

3. The endo-$\beta$-glucuronidase of claim 1 wherein the leech is of the genera Hirudinaria or Poecilobdella.

4. The endo-$\beta$-glucuronidase of claim 1 wherein the endo-$\beta$-glucuronidase is derived from the tissue of the species *Hirudinaria manillensis* or *Poecilobdella granulosa*.

5. A method for the preparation of an endo-β-glucuronidase, which comprises extracting tissue from leeches of the sub-family Hirudinariinae with ammonium sulphate solution, separating ammonium sulphate from the resulting extract, and concentrating or dehydrating the extract.

6. A pharmaceutical or verterinary formulation comprising a pharmacologically active material and a hyaluronic acid-specific endo-β-glucuronidase as spreading or percutaneous factor therefor.

7. The formulation of claim 6 wherein the endo-β-glucuronidase is derived from the leech of the sub-family Hirudinariinae.

8. The formulation of claim 6 wherein the endo-β-glucuronidase has a molecular weight in non-reduced form of 28,500±3,000 when measured by sodium dodecyl sulphate-polyacrylamide electrophoresis.

9. The formulation of claim 6 wherein the endo-β-glucuronidase is capable of cleaving hyaluronic acid, but not chondroitin, chondroitin-4-sulphate, or chondroitin-6-sulphate and retains at least 55% of its activity in an aqueous medium at pH 3.5.

10. A pharmacologically active material which comprises a pharmacologically pure extract of the leech of the sub-family Hirudinariinae and a carrier, diluent or excipient.

11. A pharmacologically active material which comprises a hyaluronic acid-specific endo-β-glucuronidase capable of cleaving hyaluronic acid, but not chondroitin, choindroitin-4-sulphate, or chondroitin-6-sulphate and having a molecular weight in non-reduced form of 28,500±3,000 when measured by sodium dodecyl sulphate-polyacrylamide electrophoresis, said endo-β-glucuronidase being such that it retains at least 70% of its activity at 37° C. after having been incubated for 30 minutes at 50° C. and at least 55% of its activity in an aqueous medium at pH 3.5; and a carrier, diluent, or excipient.

12. A method for stimulating the flow of physiological fluids which comprises contacting a physiological fluid of the body with an endo-β-glucuronidase capable of cleaving hyaluronic acid, the amount of said endo-β-glucuronidase being sufficient to stimulate the flow of said fluid.

13. The method of claim 12 wherein the endo-β-glucuronidase is derived from a leech of the sub-family Hirudinariinae.

14. The method of claim 12 wherein the endo-β-glucuronidase does not cleave chrondroitin, chondroitin-4-sulphate, or chondroitin-6-sulphate and retains at least 55% of its activity in an aqueous medium at pH 3.5.

15. The method of claim 12 wherein the physiological fluid of the eye is contacted.

16. The method of claim 12 wherein the physiological fluid of the eyes is contacted for the treatment of glaucoma, thrombosis, detached or impending detached retina, or for the non-surgical removal of obstructions.

17. The method of claim 12 wherein the physiological fluid is the blood and the blood is stimulated to reduce acute myocardial ischaemia or infarction.

* * * * *